United States Patent [19]

Bott

[11] Patent Number: 5,053,528

[45] Date of Patent: Oct. 1, 1991

[54] NOVEL DIHYDROXY COMPOUNDS WITH ESTER GROUPS AND PREPARATION THEREOF

[75] Inventor: Kaspar Bott, Mannheim, Fed. Rep. of Germany

[73] Assignee: BASF Aktiengesellschaft, Ludwigshafen, Fed. Rep. of Germany

[21] Appl. No.: 402,227

[22] Filed: Sep. 5, 1989

[30] Foreign Application Priority Data

Sep. 17, 1988 [DE] Fed. Rep. of Germany ....... 3831681

[51] Int. Cl.$^5$ ............................................. C07C 69/675
[52] U.S. Cl. ..................................... 560/189; 560/179
[58] Field of Search ............................... 560/174, 189

[56] References Cited

U.S. PATENT DOCUMENTS

| | | | |
|---|---|---|---|
| 2,350,360 | 6/1944 | Loder et al. | 560/189 |
| 2,366,667 | 1/1945 | Deebel | 560/189 |
| 2,526,554 | 10/1950 | Gresham et al. | 560/179 |
| 3,489,794 | 1/1970 | Cope | 560/189 |
| 3,499,028 | 3/1970 | McTeer | 560/189 |
| 4,359,478 | 11/1982 | Schmolka | 560/189 |

OTHER PUBLICATIONS

Chem. Abst., vol. 101, #110375n (1984).
Perner et al., Chem. Abst., vol. 92, #217055f (1980).
Perner et al., Chem. Abst., vol. 92, #182876v (1980).
Perner et al., Chem. Abst., vol. 29, #182,884 (1980).

*Primary Examiner*—James H. Reamer
*Attorney, Agent, or Firm*—William G. Conger

[57] ABSTRACT

Ester group-containing dihydroxy compounds of reduced reactivity for use in polyurethane chemistry have the formula I

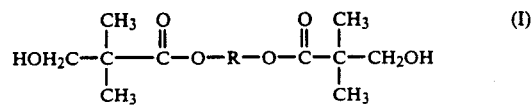

where R is linear or branched alkylene of from 2 to 20 carbon atoms, substituted or unsubstituted cycloalkylene of from 5 to 10 carbon atoms or polyoxyalkylene of from 2 to 50 oxyalkylene groups in a random or blockwise arrangement and having from 2 to 4 carbon atoms in the alkylene radical, and are prepared by transesterification of alkyl hydroxypivalates with alkanediols, cycloalkanediols or polyoxyalkylene glycols.

1 Claim, No Drawings

NOVEL DIHYDROXY COMPOUNDS WITH ESTER GROUPS AND PREPARATION THEREOF

The present invention relates to ester group-containing dihydroxy compounds of the formula I

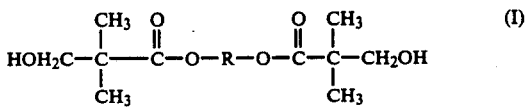

which, owing to the steric shielding of the hydroxyl groups, show reduced reactivity, and to a process for preparing same.

Polyhydroxy compounds, for example high molecular weight polyester- or polyether-polyols, and low molecular weight polyhydric alcohols are of great technical importance as formative components for preparing polyurethanes. By appropriate selection from these compounds on the basis of their chemical structure, functionality and molecular weights and as a function of the chosen mixing ratios and perhaps other factors in certain circumstances, it is possible, in conjunction with organic polyisocyanates, to prepare tailormade polyisocyanate polyaddition products, for example polyurethanes, polyureas or polyisocyanurates, having a wide range of mechanical properties.

The course of the reaction is crucially affected not only for example by catalytic or autocatalytic factors, the reaction temperature and the concentration ratios of competing reactants but also in particular by the reactivity of compounds which react with the NCO groups. This reactivity is in general determined by the basicity of the compounds, and decreases in the order aliphatic amines, aromatic amines, aliphatic ureas, primary alcohols, secondary alcohols, water and aromatic ureas. For instance, the reaction rates of primary to secondary to tertiary alcohols are in an approximate ratio of 1:0.3:0.005. However, the reactivity of the addenda, for example the dihydroxy compound, and the mechanical properties of the polyisocyanate polyaddition products prepared therefrom is also critically affected by the structural bonding of the reactive radical, for example its spatial separation and/or its steric shielding, if any. Typical representatives of dihydroxy compounds having primary hydroxyl groups and showing reduced reactivity are 2,2-dimethyl-1,3-propanediol and 3'-hydroxy-2',2'-dimethylpropyl 3-hydroxy-2,2-dimethylpropionate, the latter being obtainable from hydroxypivalaldehyde by a Tischenko reaction. However, these dihydroxy compounds have the disadvantage of a small number of bridge members between the reactive, sterically hindered hydroxyl groups.

It is also known to prepare diphenylmethane diisocyanate compositions which are liquid at room temperature.

According to DE-C-1,618,380 (U.S. Pat. No. 3,644,457), to this end one mole of 4,4'- and/or 2,4'-diphenylmethane diisocyanate—hereinafter referred to as MDI for short—is made to react with from 0.1 to 0.3 mole of tri-1,2-oxypropylene glycol and/or poly-1,2-oxypropylene glycol having a molecular weight of up to 700.

According to GB-A-1,369,334, the modification is carried out in two stages using dipropylene glycol or polyoxypropylene glycol having a molecular weight of below 2000 as modifier.

DE-A-2,913,126 (U.S. Pat. No. 4,229,347) describes MDI compositions in which from 10 to 35% by weight of the isocyanate groups are reacted with a mixture of 3 or more alkylene glycols, of which one is di-, tri- or a higher polypropylene glycol.

DE-A-2,404,166 (GB 1,430,455), by contrast, mentions mixtures of a polyoxyethylene glycol or polyoxyethylene glycol mixture having average molecular weights of less than 650 and one or more alkylene glycols of 3 or more carbon atoms as modifiers.

DE-A-2,346,996 (GB 1,377,679) concerns MDI compositions where from 10 to 35% by weight of isocyanate groups have been reacted with a commercial polyethylene glycol.

The prior art concerning the preparation of liquid polyisocyanate compositions extends beyond the use of MDI and glycols and/or polyoxyalkylene glycols to the additional use of mixtures of diphenylmethane diisocyanates and polyphenylpolymethylene polyisocyanates—hereinafter referred to as crude MDI.

According to EP-A-10,850, such a polyisocyanate composition consists of a mixture of MDI modified with polyoxyalkylenepolyols having a functionality of from 2 to 3 and being based on polyoxypropylenepolyol with or without polyoxyethylenepolyol having molecular weights of from 750 to 3000, and crude MDI.

A liquid crude MDI composition is obtained according to DE-B-2,737,338 (U.S. Pat. No. 4,055,548) by combining crude MDI with a polyoxyethylene glycol having an average molecular weight of from 200 to 600.

According to DE-B-2,624,526 (GB-B-1,550,325), a crude MDI prepared by a special process, which contains from 88 to 95% by weight of MDI, is reacted with a polyoxypropylene glycol of the molecular weight range 134–700.

DE-A-2,513,796 (GB 1,444,192) and DE-A-2,513,793 (GB 1,450,660) concern crude MDI compositions where the crude MDI has been modified with alkylene or polyoxyalkylene glycols in certain amounts.

A liquid, MDI-based polyisocyanate mixture which contains urethane groups and has an isocyanate group content of from 12 to 30% by weight is obtained according to EP-B-111,121 (U.S. Pat. No. 4,478,860) by reacting crude MDI with a polyoxypropylenepolyoxyethylenepolyol having a functionality of from 2 to 4, a hydroxyl number of from 10 to 65 and a polymerized ethylene oxide group content of from 5 to 30% by weight, based on the weight of polymerized ethylene oxide and propylene oxide groups.

It is true that the alkylene or polyoxyalkylene glycols mentioned bring about a liquefaction of the 4,4'- or 2,4'-MDI isomer melting at 42° C. or 28° C. The disadvantage, however, is that the polyisocyanate composition has only limited shelf life at around 10° C., forming crystalline precipitates thereafter. These precipitates make the polyisocyanate composition inhomogeneous and make it difficult to process it by machine.

It is also known that the nature of the modification of the MDI or crude MDI compositions have an effect on the mechanical properties of the polyurethanes prepared therefrom; that is, that to obtain a certain mechanical property in the polyurethane end product it is necessary to develop a new specific modifier.

It is an object of the present invention to develop dihydroxy compounds having spatially shielded primary hydroxyl groups of reduced reactivity where the number of bridge members between the reactive hydroxyl groups can be varied and is larger than in the above-mentioned 2,2-dimethyl-1,3-propanediol and hydroxyl- and methyl-containing propyl propionate.

We have found, surprisingly, that this object is achieved by dihydroxy compounds prepared by transesterification of alkyl hydroxypivalates with alkanediols, cycloalkanediols or oxyalkylene glycols.

The present invention accordingly provides an ester group-containing dihydroxy compound of the formula I

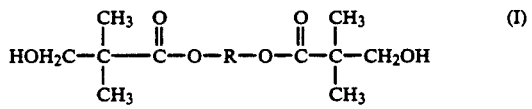

where R is linear or branched alkylene of from 2 to 20 carbon atoms, substituted or unsubstituted cycloalkylene of from 5 to 10 carbon atoms or polyoxyalkylene of from 2 to 50 oxyalkylene groups in a blockwise or random arrangement and having from 2 to 4 carbon atoms in the alkylene radical,
and a process for preparing an ester group-containing dihydroxy compound of the formula (I), which comprises transesterifying an alkyl hydroxypivalate having from 1 to 3 carbon atoms in the alkyl radical with a linear or branched alkanediol having from 2 to 20 carbon atoms in the alkylene radical, a substituted or unsubstituted cycloalkanediol having from 5 to 10 carbon atoms in the cycloalkylene radical or with a polyoxyalkylene glycol of from 2 to 50 oxyalkylene groups in a blockwise or random arrangement and having from 2 to 4 carbon atoms in the alkylene radical.

The ester group-containing dihydroxy compound according to the invention has the advantage that, by suitably choosing the radical R, it is possible to vary the physical properties, for example the compatibility, e.g. solubility or miscibility, with other polyurethane formative components, the hydrophilic or hydrophobic characteristics, the volatility, the crystallization tendency and the like, of the dihydroxy compounds in many directions and that as a result it is also possible to influence specifically the mechanical properties of the end products without significantly affecting the reactivity of the hydroxyl groups. The steric hindrance of the hydroxyl groups, as mentioned above, serves to reduce the reactivity of the primary hydroxyl groups. However, this also considerably lengthens the flow path of reaction mixtures for forming cellular or compact polyurethane elastomer moldings or foams, or it is possible to produce larger moldings.

There now follow specific observations concerning the starting materials which can be used in preparing the dihydroxy compound according to the invention and their use in polyurethane chemistry:

The dihydroxy compounds of the formula I according to the invention can be prepared by transesterifying an alkyl hydroxypivalate having from 1 to 3 carbon atoms, preferably 1 or 2 carbon atoms, in the alkyl radical, e.g. n-propyl or isopropyl hydroxypivalate, preferably ethyl hydroxypivalate, in particular methyl hydroxypivalate, with an alkanediol, a cycloalkanediol or a polyoxyalkylene glycol in the absence or preferably in the presence of a catalyst.

Suitable alkanediols advantageously have from 2 to 20 carbon atoms, preferably from 2 to 12 carbon atoms, in the branched or preferably linear alkylene radical. Examples are: 1,2-ethanediol, 1,2-propanediol, 1,3-propanediol, 2,2-dimethyl-1,3-propanediol, 1,4-butanediol, 2-methyl-1,4butanediol, 2,2-dimethyl-1,4-butanediol, 1,5-pentanediol, 2-methyl-1,5-pentanediol, 1,6-hexanediol, 2-methyl-1,6-hexanediol, 2,2-dimethyl-1,6-hexanediol, 2,2,4- and 2,4,4-trimethyl-1,6-hexanediol, 2,2,5,5-tetramethyl-1,6-hexanediol, 1,7-heptanediol, 1,8-octanediol, 2-ethyl-1,8-octanediol, 1,10-decanediol, 1,12-dodecanediol, 1,14-tetradecanediol and 1,18-octadecanediol.

It is also possible to use substituted or unsubstituted cycloalkanediols, for example cycloalkanediols having from 5 to 10 carbon atoms, preferably from 6 to 8 carbon atoms, in the cycloalkyl radical which are substituted by from 1 to 4 alkyl groups, preferably methyl groups. Possibilities are for example cyclopentanediol, 2,3-dimethyl-, 2,3,5-trimethyl- or 2,3,5,6-tetramethyl-1,4-cyclohexanediol and preferably the cyclohexanediol. isomers, in particular 1,4-cyclohexanediol.

Particularly suitable and hence preferred transesterifying agents are ether bridge-containing glycols from the group of the dialkylene glycols and polyoxyalkylene glycols of from 2 to 50 oxyalkylene groups, preferably from 2 to 20 oxyalkylene groups, in a blockwise or random arrangement which have from 2 to 4 carbon atoms in the alkylene radical. Examples are: diethylene glycol, triethylene glycol, polyoxyethylene glycols, dipropylene glycol, tripropylene glycol, polyoxypropylene glycols, dibutylene glycol, tributylene glycol, polyoxytetramethylene glycols, polyoxyethylenepolyoxypropylene glycols, polyoxyethylenepolyoxytetramethylene glycols and polyoxypropylenepolyoxytetramethylene glycols where the oxyalkylene groups are in a blockwise or random arrangement.

Polyoxyalkylene glycols of this kind can be prepared for example by anionic polymerization with alkali metal hydroxides, such as sodium hydroxide, potassium hydroxide, or alkali metal alcoholates, such as sodium methoxide, sodium ethoxide, potassium ethoxide or potassium isopropoxide, as catalysts in the presence of one or more starting molecules which contain two reactive hydrogen atoms, or by cationic polymerization with Lewis acids, such as antimony pentachloride, boron fluoride etherate and the like, or bleaching earth as catalysts from one or more alkylene oxides having from 2 to 4 carbon atoms in the alkylene radical, eg. tetrahydrofuran, 1,2-butylene oxide, 1,2-propylene oxide and ethylene oxide. Preference is given to using polyoxytetramethylene glycols having molecular weights of from 162 to 1818, preferably from 162 to 738.

As explained above, the alkyl hydroxypivalates and alkanediols, cycloalkanediols or/and polyoxyalkylene glycols can be polycondensed without a catalyst or in the presence of an esterification or preferably transesterification catalyst. Suitable esterification catalysts are for example iron, cadmium, cobalt, lead, zinc, antimony, magnesium, titanium and tin catalysts in the form of metals, metal oxides or metal salts, for example tin salts, as described for example in U.S. Pat. No. 3,162,616, tin dioctoate and/or tetrabutyl orthotitanate. Suitable transesterification catalysts are for example zinc acetate, antimony acetate, tetrabutyl orthotitanate and preferably alkali metal alcoholates, such as sodium alcoholates or potassium alcoholates.

To prepare the dihydroxy compounds of the formula (I) according to the invention, the alkyl hydroxypivalate and the alkanediol, substituted or unsubstituted cycloalkanediol and/or preferably polyoxyalkylene glycol are transesterified in a molar ratio of from 2:1 to 3:1, preferably of from 2:1 to 2.5:1, in the absence or presence of a diluent, without a catalyst or preferably in the presence of a transesterification catalyst at from 40° to 150° C., preferably at from 50° to 120° C. After the transesterification has ended, which usually requires a reaction time of from 0.5 to 10 hours, preferably from 1 to 5 hours, the excess alkyl hydroxypivalate, the alcohol formed and any diluent are distilled off, preferably under reduced pressure.

The transesterification reaction, as stated above, can be carried out in the presence of a diluent and in the presence or absence of an inert gas atmosphere, for example nitrogen, carbon monoxide, helium or argon. Examples of diluents are benzene, toluene, xylene, chlorobenzene and dichlorobenzene.

The novel ester group-containing dihydroxy compound of the formula (I)

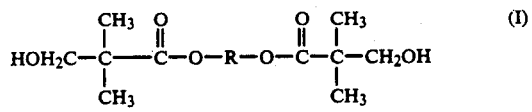

prepared by the above-described process preferably contains as the radical —R— a 1,2-ethylene, 1,2-propylene, 1,3-propylene, 2,2-dimethyl-1,3-propylene, 1,4-butylene, 2-methyl-1,4-butylene, 2,2-dimethyl-1,4-butylene, 1,5-pentamethylene, 2-methyl-1,5-pentamethylene, 1,6-hexamethylene,2-methyl-1,6-hexamethylene, 2,2-dimethyl-1,6-hexamethylene, 2,2,4-trimethyl-1,6-hexamethylene, 2,4,4-trimethyl-1,6-hexamethylene or 2,2,5,5-tetramethyl-1,6-hexamethylene radical and in particular one or more oxyalkylene units of the formula

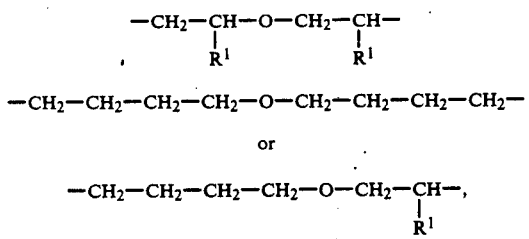

where each $R^1$, which may be identical to or different from the others, is hydrogen, methyl or ethyl.

The dihydroxy compound of the formula I according to the invention is preferably used for preparing urethane group-containing polyisocyanate mixtures which are liquid at room temperature on the basis of 4,4'-diphenylmethane diisocyanate or mixtures of 4,4'-diphenylmethane diisocyanate and other diphenylmethane diisocyanate isomers and/or polyphenylpolymethylene polyisocyanates. It is also suitable for use as a chain extender for polyisocyanate polyaddition reactions for forming for example compact or cellular urethane or urethane and urea group-containing elastomers and as a formative component for preparing high molecular weight polyesters or unsaturated polyester resins.

The 4,4'-MDI-based urethane group-containing polyisocyanate mixtures which are liquid at room temperature can be prepared in a conventional manner. By procedure, the crude MDI, which advantageously has an MDI content of from 40 to 95% by weight, preferably of from. 60 to 90% by weight, based on the total weight, is made to react at from 10° to 100° C., preferably at from 30° to 80° C., with such an amount of the dihydroxy compound of the formula (I) according to the invention that the NCO:OH group ratio is from 1:0.001 to 0.30, preferably from 1:0.01 to 0.19, in particular from 1:0.01 to 0.1. After a reaction time of from 0.5 to 6 hours, preferably of from 1 to 3 hours, the modified polyisocyanate mixture is cooled.

If the urethane group-containing polyisocyanate mixtures are predominantly used for preparing polyurethane flexible foams, the preferred procedure comprises reacting the 4,4'-MDI or preferably an MDI isomer mixture which contains from 46 to 96% by weight, preferably from 55 to 85% by weight, of 4,4'-MDI, from 54 to 2% by weight, preferably from 45 to 14% by weight, of 2,4-MDI and from 0 to 2% by weight, preferably from 0 to 1% by weight, of 2,2'-MDI, based on the total weight, and the dihydroxy compound of the formula (I) according to the invention at from 20° to 100° C., preferably at from 40° to 80° C., in such an amount that the ratio of NCO:OH groups is from 1:0.001 to 0.3, preferably from 1:0.01 to 0.2, in particular from 1:0.02 to 0.15. Following a reaction time of from 0.5 to 6 hours, preferably of from 1 to 3 hours, the urethane group-containing MDI is cooled to temperatures of from 20° to 80° C. and diluted with 4,4'-MDI, the aforementioned MDI isomer mixture or preferably a crude MDI having an MDI content of from 45 to 80% by weight, preferably of from 50 to 70% by weight, based on the total weight. If from 40 to 90 parts by weight of the urethane group-containing MDI are used, this usually requires from 60 to 10 parts by weight of 4,4'-MDI, MDI isomer mixture or crude MDI.

The liquid, urethane group-containing MDI or crude MDI mixtures advantageously have an NCO content of from 30 to 12% by weight, preferably of from 28 to 22% by weight, based on the total weight, and are used for preparing for example flexible polyurethane foams, coating materials or sports surfaces.

EXAMPLES

Preparation of ester group-containing dihydroxy compounds.

EXAMPLE 1

In a 2-1 stirred flask supporting a packed column (20 cm filled depth, 5 mm steel networks), a mixture of
1300 g (2.00 mol) of polyoxytetramethylene glycol having a molecular weight of 650 (OH number 173),
528 g (4.00 mol) of methyl hydroxypivalate having a purity of 99 % by weight and
18.8 g of potassium methoxide
was heated to 65° C. in the course of 15 minutes. The methanol formed was then distilled off overhead under reduced pressure (300 mbar).

To remove all of the methanol formed, the temperature of the reaction mixture was gradually raised from 65° C. to 105° C., and at the same time the pressure was reduced to 30 mbar. The transesterification was then completed at 105° C. under a reduced pressure of 0.3 mbar in the course of 4 hours.

The potassium salt catalyst was removed by twice stirring the esterification product with 55 g of Ambosol ® from Hoechst France each time at 100° C. and filtering off the aid.

The dihydroxy compound prepared in this way had a hydroxyl number of 127 and a potassium content of 0.0003 % by weight. The spectroscopic properties were in conformity with a structural formula I for R equal to

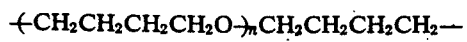

145 g of distillate were isolated, being 95% by weight of methanol and 5% by weight of methyl hydroxypivalate.

EXAMPLE 2

A mixture of 450 g (0.75 mol) of polyoxypropylene glycol having a molecular weight of 600, 198 g (1.5 mol) of methyl hydroxypivalate and 6.7 g of potassium methoxide were stirred at 65° C. in the apparatus described in Example 1 for 15 minutes.

The methanol formed was distilled off under reduced pressure, which at the start of the transesterification was 300 mbar and at the end of the reaction was 1 mbar. To complete the transesterification and distil off the remaining methanol, the reaction mixture was heated at 100° C. under 1 mbar for 3 hours.

The catalyst was removed as described in Example 1.

The dihydroxy compound obtained had a hydroxyl number of 140 and a residual potassium content of 0.15 % by weight. The spectroscopic properties were in conformity with the structural formula I for R equal to

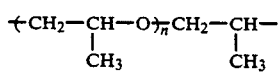

Preparation of urethane group-containing polyisocyanate mixtures based on 4,4'-MDI

EXAMPLE 3

76.1 parts by weight of the dihydroxy compound prepared as in Example 2, which had a hydroxyl number of 140, were added to a mixture of 102 parts by weight of 4,4'-MDI and 83 parts by weight of 2,4'-MDI at 70° C. with stirring.

Following a reaction time of 2 hours at 70° C., the urethane group-containing MDI was cooled down to room temperature and diluted with 227.5 parts by weight of crude MDI having an NCO content of 31 % by weight.

The polyisocyanate mixture obtained had an NCO content of 25.8 % by weight and did not produce any sediment on being stored at 3° C. for 14 days.

EXAMPLE 4

76.1 parts by weight of the dihydroxy compound obtained as in Example 2, which had a hydroxyl number of 140, were added to a mixture of 102 parts by weight of 4,4'-MDI 83 parts by weight of 2,4'-MDI and 227.5 parts by weight of crude MDI having an MDI isomer, content of 44% by weight at 50° C. with stirring.

After a reaction time of 2 hours at 70° C., the urethane group-containing polyisocyanate mixture was cooled down to room temperature. The product had an NCO content of 25.9% by weight and did not produce any sediment on being stored at −3° C. for 14 days.

I claim:

1. An ester group-containing dihydroxy compound of the formula I

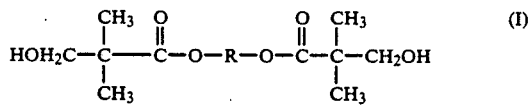

where R is polyoxyalkylene of from 2 to 50 oxyalkylene groups in a blockwise or random arrangement and having from 2 to 4 carbon atoms in the alkylene radical.

* * * * *